United States Patent [19]

Williams

[11] Patent Number: 5,376,367
[45] Date of Patent: Dec. 27, 1994

[54] FUSION PROTEINS COMPRISING MGF AND IL-3

[75] Inventor: Douglas E. Williams, Redmond, Wash.

[73] Assignee: Immunex Corporation, Seattle, Wash.

[21] Appl. No.: 797,553

[22] Filed: Nov. 22, 1991

[51] Int. Cl.$^5$ .................. A61K 45/05; C12P 21/06; C07K 13/00
[52] U.S. Cl. .................. 424/85.2; 435/69.7; 435/69.52; 530/350; 530/351; 530/402; 424/85.1
[58] Field of Search ............... 435/69.7, 69.52, 69.5; 935/47; 530/350, 351, 402, 403; 424/85.1, 85.2

[56] References Cited

FOREIGN PATENT DOCUMENTS

| 0275598 | 12/1987 | European Pat. Off. . |
| 0282185 | 2/1988 | European Pat. Off. . |
| 0288809 | 9/1988 | European Pat. Off. . |
| WO8502863 | 12/1984 | WIPO . |

OTHER PUBLICATIONS

Tsuji et al. *J. Cell Physiol.* Sep. 1991, 148(3):362–9 [abstract only].

Broxmeyer et al., *J. Exp. Med.* Aug. 1, 1991, 174(2)447–458 [abstract only].

Martin et al., "Primary Structure and Functional Expression of Rat and Human Stem Cell Factor DNAs", *Cell* 63:203 (Oct. 1990).

Curtis et al., "Enhanced hematopoietic activity of a human granulocyte/macrophage colony-stimulating factor—interleukin 3 fusion protein", *Proc. Natl. Acad. Sci. USA*, 88:5809 (Jul. 1991).

Williams et al., "Identification of a Ligand for the c—kit Proto-Oncogene", *Cell* 63:167 (Oct. 1990).

Anderson et al., "Molecular Cloning of Mast Cell Growth Factor, a Hematopoietin That is Active in Both Membrane Bound and Soluble Forms", *Cell* 63:235 (Oct. 1990).

Zsebo et al., "Identification, Purification, and Biological Characterization of Hematopoietic Stem Cell Factor from Buffalo Rat Liver-Conditioned Medium", *Cell* 63:195 (Oct. 1990).

*Primary Examiner*—Robert A. Wax
*Assistant Examiner*—Keith D. Hendricks
*Attorney, Agent, or Firm*—Patricia Anne Perkins; Scott G. Hallquist; Christopher L. Wight

[57] ABSTRACT

A fusion protein which comprises MGF and IL-3. Such fusion proteins have enhanced biological activity.

6 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 906 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
( B ) CLONE: PIXY521

( i x ) FEATURE:
( A ) NAME/KEY: matpeptide
( B ) LOCATION: 1..903

( i x ) FEATURE:
( A ) NAME/KEY: CDS
( B ) LOCATION: 1..906

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| GCT | CCC | ATG | ACC | CAG | ACG | ACG | CCC | TTG | AAG | ACC | AGC | TGG | GTT | GAT | TGC | 48 |
| Ala | Pro | Met | Thr | Gln | Thr | Thr | Pro | Leu | Lys | Thr | Ser | Trp | Val | Asp | Cys | |
| 1 | | | | 5 | | | | | 10 | | | | | 15 | | |
| TCT | AAC | ATG | ATC | GAT | GAA | ATT | ATA | ACA | CAC | TTA | AAG | CAG | CCA | CCT | TTG | 96 |
| Ser | Asn | Met | Ile | Asp | Glu | Ile | Ile | Thr | His | Leu | Lys | Gln | Pro | Pro | Leu | |
| | | | 20 | | | | | 25 | | | | | 30 | | | |
| CCT | TTG | CTG | GAC | TTC | AAC | AAC | CTC | AAT | GGG | GAA | GAC | CAA | GAC | ATT | CTG | 144 |
| Pro | Leu | Leu | Asp | Phe | Asn | Asn | Leu | Asn | Gly | Glu | Asp | Gln | Asp | Ile | Leu | |
| | | 35 | | | | | 40 | | | | | 45 | | | | |
| ATG | GAA | AAT | AAC | CTT | CGA | AGG | CCA | AAC | CTG | GAG | GCA | TTC | AAC | AGG | GCT | 192 |
| Met | Glu | Asn | Asn | Leu | Arg | Arg | Pro | Asn | Leu | Glu | Ala | Phe | Asn | Arg | Ala | |
| | 50 | | | | | 55 | | | | | 60 | | | | | |
| GTC | AAG | AGT | TTA | CAG | GAC | GCA | TCA | GCA | ATT | GAG | AGC | ATT | CTT | AAA | AAT | 240 |
| Val | Lys | Ser | Leu | Gln | Asp | Ala | Ser | Ala | Ile | Glu | Ser | Ile | Leu | Lys | Asn | |
| 65 | | | | | 70 | | | | | 75 | | | | | 80 | |
| CTC | CTG | CCA | TGT | CTG | CCC | CTG | GCC | ACG | GCC | GCA | CCC | ACG | CGA | CAT | CCA | 288 |
| Leu | Leu | Pro | Cys | Leu | Pro | Leu | Ala | Thr | Ala | Ala | Pro | Thr | Arg | His | Pro | |
| | | | | 85 | | | | | 90 | | | | | 95 | | |
| ATC | CAT | ATC | AAG | GAC | GGT | GAC | TGG | AAT | GAA | TTC | CGG | AGG | AAA | CTG | ACG | 336 |
| Ile | His | Ile | Lys | Asp | Gly | Asp | Trp | Asn | Glu | Phe | Arg | Arg | Lys | Leu | Thr | |
| | | | 100 | | | | | 105 | | | | | 110 | | | |
| TTC | TAT | CTG | AAA | ACC | CTT | GAG | AAT | GCG | CAG | GCT | CAA | CAG | ACG | ACT | TTG | 384 |
| Phe | Tyr | Leu | Lys | Thr | Leu | Glu | Asn | Ala | Gln | Ala | Gln | Gln | Thr | Thr | Leu | |
| | | 115 | | | | | 120 | | | | | 125 | | | | |
| AGC | CTC | GCG | ATC | TTT | GGT | GGC | GGT | GGA | TCC | GGC | GGT | GGC | GGC | GGC | TCA | 432 |
| Ser | Leu | Ala | Ile | Phe | Gly | Gly | Gly | Gly | Ser | Gly | Gly | Gly | Gly | Gly | Ser | |
| | 130 | | | | | 135 | | | | | 140 | | | | | |
| GAA | GGG | ATC | TGC | AGG | AAT | CGT | GTG | ACT | AAT | AAC | GTA | AAA | GAC | GTC | ACT | 480 |
| Glu | Gly | Ile | Cys | Arg | Asn | Arg | Val | Thr | Asn | Asn | Val | Lys | Asp | Val | Thr | |
| 145 | | | | | 150 | | | | | 155 | | | | | 160 | |
| AAA | TTG | GTG | GCA | AAT | CTT | CCA | AAA | GAC | TAC | ATG | ATA | ACC | CTC | AAA | TAT | 528 |
| Lys | Leu | Val | Ala | Asn | Leu | Pro | Lys | Asp | Tyr | Met | Ile | Thr | Leu | Lys | Tyr | |
| | | | | 165 | | | | | 170 | | | | | 175 | | |
| GTC | CCC | GGG | ATG | GAT | GTT | TTG | CCA | AGT | CAT | TGT | TGG | ATA | AGC | GAG | ATG | 576 |
| Val | Pro | Gly | Met | Asp | Val | Leu | Pro | Ser | His | Cys | Trp | Ile | Ser | Glu | Met | |
| | | | 180 | | | | | 185 | | | | | 190 | | | |
| GTA | GTA | CAA | TTG | TCA | GAC | AGC | TTG | ACT | GAT | CTT | CTG | GAC | AAG | TTT | TCA | 624 |
| Val | Val | Gln | Leu | Ser | Asp | Ser | Leu | Thr | Asp | Leu | Leu | Asp | Lys | Phe | Ser | |
| | | 195 | | | | | 200 | | | | | 205 | | | | |
| AAT | ATT | TCT | GAA | GGC | TTG | AGT | AAT | TAT | TCC | ATC | ATA | GAC | AAA | CTT | GTG | 672 |
| Asn | Ile | Ser | Glu | Gly | Leu | Ser | Asn | Tyr | Ser | Ile | Ile | Asp | Lys | Leu | Val | |
| | 210 | | | | | 215 | | | | | 220 | | | | | |
| AAT | ATA | GTG | GAT | GAC | CTT | GTG | GAG | TGC | GTG | AAA | GAA | AAC | TCA | TCT | AAG | 720 |
| Asn | Ile | Val | Asp | Asp | Leu | Val | Glu | Cys | Val | Lys | Glu | Asn | Ser | Ser | Lys | |
| 225 | | | | | 230 | | | | | 235 | | | | | 240 | |
| GAT | CTA | AAA | AAA | TCA | TTC | AAG | AGC | CCA | GAA | CCC | AGG | CTC | TTT | ACT | CCT | 768 |
| Asp | Leu | Lys | Lys | Ser | Phe | Lys | Ser | Pro | Glu | Pro | Arg | Leu | Phe | Thr | Pro | |
| | | | | 245 | | | | | 250 | | | | | 255 | | |
| GAA | GAA | TTC | TTT | AGA | ATT | TTT | AAT | AGA | TCC | ATT | GAT | GCC | TTC | AAG | GAC | 816 |
| Glu | Glu | Phe | Phe | Arg | Ile | Phe | Asn | Arg | Ser | Ile | Asp | Ala | Phe | Lys | Asp | |

```
                              260                        265                          270
TTT  GTA  GTG  GCA  TCT  GAA  ACT  AGT  GAT  TGT  GTG  GTT  TCT  TCA  ACA  TTA           864
Phe  Val  Val  Ala  Ser  Glu  Thr  Ser  Asp  Cys  Val  Val  Ser  Ser  Thr  Leu
          275                      280                     285

AGT  CCT  GAG  AAA  GGG  AAG  GCC  AAA  AAT  CCC  CCT  GGA  GAC  TAA                     906
Ser  Pro  Glu  Lys  Gly  Lys  Ala  Lys  Asn  Pro  Pro  Gly  Asp
     290                      295                     300
```

( 2 ) INFORMATION FOR SEQ ID NO:2:

( i ) SEQUENCE CHARACTERISTICS:
    ( A ) LENGTH: 301 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Ala  Pro  Met  Thr  Gln  Thr  Thr  Pro  Leu  Lys  Thr  Ser  Trp  Val  Asp  Cys
 1              5                     10                           15

Ser  Asn  Met  Ile  Asp  Glu  Ile  Ile  Thr  His  Leu  Lys  Gln  Pro  Pro  Leu
               20                      25                     30

Pro  Leu  Leu  Asp  Phe  Asn  Asn  Leu  Asn  Gly  Glu  Asp  Gln  Asp  Ile  Leu
          35                      40                     45

Met  Glu  Asn  Asn  Leu  Arg  Arg  Pro  Asn  Leu  Glu  Ala  Phe  Asn  Arg  Ala
     50                       55                     60

Val  Lys  Ser  Leu  Gln  Asp  Ala  Ser  Ala  Ile  Glu  Ser  Ile  Leu  Lys  Asn
 65                      70                     75                          80

Leu  Leu  Pro  Cys  Leu  Pro  Leu  Ala  Thr  Ala  Ala  Pro  Thr  Arg  His  Pro
               85                      90                          95

Ile  His  Ile  Lys  Asp  Gly  Asp  Trp  Asn  Glu  Phe  Arg  Arg  Lys  Leu  Thr
               100                     105                    110

Phe  Tyr  Leu  Lys  Thr  Leu  Glu  Asn  Ala  Gln  Ala  Gln  Gln  Thr  Thr  Leu
          115                     120                    125

Ser  Leu  Ala  Ile  Phe  Gly  Gly  Gly  Ser  Gly  Gly  Gly  Gly  Gly  Gly  Ser
     130                     135                    140

Glu  Gly  Ile  Cys  Arg  Asn  Arg  Val  Thr  Asn  Asn  Val  Lys  Asp  Val  Thr
145                      150                    155                         160

Lys  Leu  Val  Ala  Asn  Leu  Pro  Lys  Asp  Tyr  Met  Ile  Thr  Leu  Lys  Tyr
                    165                     170                    175

Val  Pro  Gly  Met  Asp  Val  Leu  Pro  Ser  His  Cys  Trp  Ile  Ser  Glu  Met
               180                     185                    190

Val  Val  Gln  Leu  Ser  Asp  Ser  Leu  Thr  Asp  Leu  Leu  Asp  Lys  Phe  Ser
          195                     200                    205

Asn  Ile  Ser  Glu  Gly  Leu  Ser  Asn  Tyr  Ser  Ile  Ile  Asp  Lys  Leu  Val
     210                     215                    220

Asn  Ile  Val  Asp  Asp  Leu  Val  Glu  Cys  Val  Lys  Glu  Asn  Ser  Ser  Lys
225                      230                    235                         240

Asp  Leu  Lys  Lys  Ser  Phe  Lys  Ser  Pro  Glu  Pro  Arg  Leu  Phe  Thr  Pro
                    245                     250                    255

Glu  Glu  Phe  Phe  Arg  Ile  Phe  Asn  Arg  Ser  Ile  Asp  Ala  Phe  Lys  Asp
               260                     265                    270

Phe  Val  Val  Ala  Ser  Glu  Thr  Ser  Asp  Cys  Val  Val  Ser  Ser  Thr  Leu
          275                     280                    285

Ser  Pro  Glu  Lys  Gly  Lys  Ala  Lys  Asn  Pro  Pro  Gly  Asp
     290                     295                    300
```

( 2 ) INFORMATION FOR SEQ ID NO:3:

( i ) SEQUENCE CHARACTERISTICS:
    ( A ) LENGTH: 912 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Homo sapiens ( v i i ) IMMEDIATE SOURCE:
    ( B ) CLONE: PIXY523

( i x ) FEATURE:
    ( A ) NAME/KEY: CDS
    ( B ) LOCATION: 1..912

( i x ) FEATURE:
    ( A ) NAME/KEY: matpeptide
    ( B ) LOCATION: 1..909

( x i ) SEQUENCE DESCRIPTION: SEQ ID NO:3:

```
GAA GGG ATC TGC AGG AAT CGT GTG ACT AAT AAT GTA AAA GAC GTC ACT        48
Glu Gly Ile Cys Arg Asn Arg Val Thr Asn Asn Val Lys Asp Val Thr
 1               5                  10                  15

AAA TTG GTG GCA AAT CTT CCA AAA GAC TAC ATG ATA ACC CTC AAA TAT        96
Lys Leu Val Ala Asn Leu Pro Lys Asp Tyr Met Ile Thr Leu Lys Tyr
            20                  25                  30

GTC CCC GGG ATG GAT GTT TTG CCA AGT CAT TGT TGG ATA AGC GAG ATG       144
Val Pro Gly Met Asp Val Leu Pro Ser His Cys Trp Ile Ser Glu Met
        35                  40                  45

GTA GTA CAA TTG TCA GAC AGC TTG ACT GAT CTT CTG GAC AAG TTT TCA       192
Val Val Gln Leu Ser Asp Ser Leu Thr Asp Leu Leu Asp Lys Phe Ser
    50                  55                  60

AAT ATT TCT GAA GGC TTG AGT AAT TAT TCC ATC ATA GAC AAA CTT GTG       240
Asn Ile Ser Glu Gly Leu Ser Asn Tyr Ser Ile Ile Asp Lys Leu Val
65                  70                  75                  80

AAT ATA GTG GAT GAC CTT GTG GAG TGC GTG AAA GAA AAC TCA TCT AAG       288
Asn Ile Val Asp Asp Leu Val Glu Cys Val Lys Glu Asn Ser Ser Lys
                85                  90                  95

GAT CTA AAA AAA TCA TTC AAG AGC CCA GAA CCC AGG CTC TTT ACT CCT       336
Asp Leu Lys Lys Ser Phe Lys Ser Pro Glu Pro Arg Leu Phe Thr Pro
            100                 105                 110

GAA GAA TTC TTT AGA ATT TTT AAT AGA TCC ATT GAT GCC TTC AAG GAC       384
Glu Glu Phe Phe Arg Ile Phe Asn Arg Ser Ile Asp Ala Phe Lys Asp
        115                 120                 125

TTT GTA GTG GCA TCT GAA ACT AGT GAT TGT GTG GTT TCT TCA ACA TTA       432
Phe Val Val Ala Ser Glu Thr Ser Asp Cys Val Val Ser Ser Thr Leu
    130                 135                 140

AGT CCT GAG AAA GGG AAG GCC AAA AAT CCC CCT GGA GAC GGG GCC GGC       480
Ser Pro Glu Lys Gly Lys Ala Lys Asn Pro Pro Gly Asp Gly Ala Gly
145                 150                 155                 160

GGG GCC GGA TCC GGG GGT GGC GGC GGC TCA GCT CCC ATG ACC CAG ACG       528
Gly Ala Gly Ser Gly Gly Gly Gly Gly Ser Ala Pro Met Thr Gln Thr
                165                 170                 175

ACG CCC TTG AAG ACC AGC TGG GTT GAT TGC TCT AAC ATG ATC GAT GAA       576
Thr Pro Leu Lys Thr Ser Trp Val Asp Cys Ser Asn Met Ile Asp Glu
            180                 185                 190

ATT ATA ACA CAC TTA AAG CAG CCA CCT TTG CCT TTG CTG GAC TTC AAC       624
Ile Ile Thr His Leu Lys Gln Pro Pro Leu Pro Leu Leu Asp Phe Asn
        195                 200                 205

AAC CTC AAT GGG GAA GAC CAA GAC ATT CTG ATG GAA AAT AAC CTT CGA       672
Asn Leu Asn Gly Glu Asp Gln Asp Ile Leu Met Glu Asn Asn Leu Arg
```

|  |  |  |  |  |  |  |  |  |  |  |  |  |  |  |
|---|---|---|---|---|---|---|---|---|---|---|---|---|---|---|
| 210 | | | | | 215 | | | | | 220 | | | | |
| AGG | CCA | AAC | CTG | GAG | GCA | TTC | AAC | AGG | GCT | GTC | AAG | AGT | TTA | CAG | GAC | 720
| Arg | Pro | Asn | Leu | Glu | Ala | Phe | Asn | Arg | Ala | Val | Lys | Ser | Leu | Gln | Asp |
| 225 | | | | 230 | | | | | 235 | | | | | 240 |
| GCA | TCA | GCA | ATT | GAG | AGC | ATT | CTT | AAA | AAT | CTC | CTG | CCA | TGT | CTG | CCC | 768
| Ala | Ser | Ala | Ile | Glu | Ser | Ile | Leu | Lys | Asn | Leu | Leu | Pro | Cys | Leu | Pro |
| | | | | 245 | | | | | 250 | | | | | 255 |
| CTG | GCC | ACG | GCC | GCA | CCC | ACG | CGA | CAT | CCA | ATC | CAT | ATC | AAG | GAC | GGT | 816
| Leu | Ala | Thr | Ala | Ala | Pro | Thr | Arg | His | Pro | Ile | His | Ile | Lys | Asp | Gly |
| | | | 260 | | | | | 265 | | | | | 270 | |
| GAC | TGG | AAT | GAA | TTC | CGG | AGG | AAA | CTG | ACG | TTC | TAT | CTG | AAA | ACC | CTT | 864
| Asp | Trp | Asn | Glu | Phe | Arg | Arg | Lys | Leu | Thr | Phe | Tyr | Leu | Lys | Thr | Leu |
| | | 275 | | | | | 280 | | | | | 285 | | |
| GAG | AAT | GCG | CAG | GCT | CAA | CAG | ACG | ACT | TTG | AGC | CTC | GCG | ATC | TTT | TGA | 912
| Glu | Asn | Ala | Gln | Ala | Gln | Gln | Thr | Thr | Leu | Ser | Leu | Ala | Ile | Phe | |
| 290 | | | | | 295 | | | | | 300 | | | | | |

( 2 ) INFORMATION FOR SEQ ID NO:4:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Glu Gly Ile Cys Arg Asn Arg Val Thr Asn Asn Val Lys Asp Val Thr
  1               5                  10                  15

Lys Leu Val Ala Asn Leu Pro Lys Asp Tyr Met Ile Thr Leu Lys Tyr
             20                  25                  30

Val Pro Gly Met Asp Val Leu Pro Ser His Cys Trp Ile Ser Glu Met
         35                  40                  45

Val Val Gln Leu Ser Asp Ser Leu Thr Asp Leu Leu Asp Lys Phe Ser
     50                  55                  60

Asn Ile Ser Glu Gly Leu Ser Asn Tyr Ser Ile Ile Asp Lys Leu Val
 65                  70                  75                  80

Asn Ile Val Asp Asp Leu Val Glu Cys Val Lys Glu Asn Ser Ser Lys
                 85                  90                  95

Asp Leu Lys Lys Ser Phe Lys Ser Pro Glu Pro Arg Leu Phe Thr Pro
                100                 105                 110

Glu Glu Phe Phe Arg Ile Phe Asn Arg Ser Ile Asp Ala Phe Lys Asp
            115                 120                 125

Phe Val Val Ala Ser Glu Thr Ser Asp Cys Val Val Ser Ser Thr Leu
    130                 135                 140

Ser Pro Glu Lys Gly Lys Ala Lys Asn Pro Pro Gly Asp Gly Ala Gly
145                 150                 155                 160

Gly Ala Gly Ser Gly Gly Gly Gly Ser Ala Pro Met Thr Gln Thr
                165                 170                 175

Thr Pro Leu Lys Thr Ser Trp Val Asp Cys Ser Asn Met Ile Asp Glu
            180                 185                 190

Ile Ile Thr His Leu Lys Gln Pro Pro Leu Pro Leu Leu Asp Phe Asn
        195                 200                 205

Asn Leu Asn Gly Glu Asp Gln Asp Ile Leu Met Glu Asn Asn Leu Arg
    210                 215                 220

Arg Pro Asn Leu Glu Ala Phe Asn Arg Ala Val Lys Ser Leu Gln Asp
225                 230                 235                 240

Ala Ser Ala Ile Glu Ser Ile Leu Lys Asn Leu Leu Pro Cys Leu Pro
                245                 250                 255
```

```
Leu Ala Thr Ala Ala Pro Thr Arg His Pro Ile His Ile Lys Asp Gly
            260                 265                 270

Asp Trp Asn Glu Phe Arg Arg Lys Leu Thr Phe Tyr Leu Lys Thr Leu
        275                 280                 285

Glu Asn Ala Gln Ala Gln Gln Thr Thr Leu Ser Leu Ala Ile Phe
    290                 295                 300
```

FUSION PROTEINS COMPRISING MGF AND IL-3

BACKGROUND OF THE INVENTION

The present invention relates to fusion proteins for stimulating growth of hematopoietic cells, and more particularly to the construction of fusion proteins comprising MGF and IL-3.

Hematopoietic growth factors (or hematopoietins) regulate the growth and maturation of various lineages of blood cells. All blood cells are believed to develop from a single class of precursor cells called stem cells. Each hematopoietin causes specific classes of blood cells to differentiate and proliferate. When a stem cell divides in the bone marrow, it can replicate itself as a stem cell or become committed to a particular developmental pathway. As a result of commitment to a particular developmental pathway, a stem cell displays receptors on its cell surface that enables it to respond to certain hormonal signals. Such signals push the cell further down a pathway leading to terminal differentiation.

A number of hematopoietins have been identified which regulate cell development at various levels within the hematopoietic stem and progenitor cell hierarchy. The majority of growth factors that have been identified influence relatively late stages of differentiation and regulate the number and function of mature differentiated hematopoietic elements. Interleukin-3 ("IL-3" or "multi-CSF)), for example, stimulates formation of a broad range of hematopoietic cells, including granulocytes, macrophages, eosinophils, mast cells, megakaryocytes and erythroid cells. IL-3 has been identified, isolated and molecularly cloned (EP Publ. Nos. 275,598 and 282,185). Recently, a Mast Cell Growth Factor "MGF"), which controls very early progenitors in the hematopoietic hierarchy, has been identified, isolated and molecularly cloned (Williams et al., *Cell* 63:167, 1991; Anderson et al., *Cell* 63:235, 1991).

Preclinical studies indicate that such hematopoietins may be useful in treating various cytopenias, potentiating immune responsiveness to infectious pathogens, and assisting in reconstituting normal blood cell populations following viral infection or radiation or chemotherapy-induced hematopoietic cell suppression. MGF, in particular, because of its early effect on hematopoietic cells, is likely to be useful for treating a plastic anemia. In order to determine their optimal therapeutic potential, the effect of various combinations of such proteins on hematopoietic cells has been the subject of considerable study.

SUMMARY OF THE INVENTION

The present invention relates to fusion proteins comprising MGF and IL-3. The fusion proteins preferably have a formula selected from the group consisting of $$R_1-R_2, R_2-R_1, R_1-L-R_2 \text{ and } R_2-L-R_1$$

wherein $R_1$ is MGF; $R_2$ is IL-3; and L is a linker peptide sequence. In the most preferred aspects of the present invention, MGF and IL-3 are linked together via a linker sequence which permits folding of the MGF or IL-3 domains in such a manner as to preserve the ability of each domain to bind to its respective cell surface receptor molecule.

The fusion proteins of the present invention show enhanced ability to stimulate human bone marrow cells than MGF or IL-3 alone or in combination.

DETAILED DESCRIPTION OF THE INVENTION

The present invention is directed to fusion proteins comprising MGF and IL-3. The following terms are defined as follows:

"Recombinant," as used herein, means that a protein is derived from recombinant (e.g., microbial or mammalian) expression systems. "Microbial" refers to recombinant proteins made in bacterial or fungal (e.g., yeast) expression systems. As a product. "recombinant microbial" defines a protein produced in a microbial expression system which is essentially free of native endogenous substances. Protein expressed in most bacterial cultures. e.g., *E. coli,* will be free of glycan. Protein expressed in yeast may have a glycosylation pattern different from that expressed in mammalian cells.

"Biologically active," as used throughout the specification means that a particular molecule shares sufficient amino acid sequence similarity with native forms so as to be capable of binding to native receptor, transmitting a stimulus to a cell, or cross-reacting antibodies raised against the particular molecule.

"DNA sequence" refers to a DNA polymer, in the form of a separate fragment or as a component of a larger DNA construct. Preferably, the DNA sequences are in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences, or introns, which are typically present in eukaryotic genes. Genomic DNA containing the relevant sequences could also be used. Sequences of non-translated DNA may be present 5' or 3' from the open reading frame, where the same do not interfere with manipulation or expression of the coding regions.

"Nucleotide sequence" refers to a heteropolymer of deoxyribonucleotides. DNA sequences encoding the proteins provided of this invention can be assembled from cDNA fragments and short oligonucleotide linkers, or from a series of oligonucleotides, to provide a synthetic gene which is capable of being expressed in a recombinant transcriptional unit.

"Recombinant expression vector" refers to a replicable DNA construct used either to amplify or to express DNA which encodes the fusion proteins of the present invention and which includes a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription and translation initiation and termination sequences. Structural elements intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally be subsequently cleaved from the expressed recombinant protein to provide a final product. "Recombinant microbial expression system" means a substantially homogeneous monoculture of suitable host microorganisms, for example, bacteria such as *E. coli* or yeast such as *S. cerevisiae*, which have stably integrated a recombinant transcriptional unit into chromosomal DNA or carry the recombinant transcriptional unit as a component of a resident plasmid. Generally, cells constituting the system are the progeny of a single ancestral transformant. Recombinant expression systems as defined herein will express heterologous protein upon induction of the regulatory elements linked to the DNA sequence or synthetic gene to be expressed.

MAST CELL GROWTH FACTOR

The term mast cell growth factor ("MGF") refers to proteins having substantially the same characteristics of MGF in that they are capable of binding to receptors for MGF or transducing a biological signal initiated by binding to MGF receptors, or cross-reacting with anti-MGF antibodies raised against MGF. MGF includes a family of mammalian polypeptides which are capable of stimulating IL-3 dependent mast cell lines and hematopoietic progenitor cells, and serve as a ligand for the gene product of the c-kit proto-oncogene. MGF polypeptides and DNA sequences encoding MGF polypeptides are disclosed, for example, in Anderson et al., *Cell* 63:235, 1991; Martin et al., *Cell* 65:203, 1991; and EP-A-0 423 980. As used herein, the term MGF includes analogs or subunits of native mammalian polypeptides with substantially identical or substantially similar amino acid polypeptide sequences which bind to the protein expressed by the c-kit proto-oncogene and which induce proliferation of mast cells, for example, the IL-3 dependent murine mast cell line MC6 or human cell line TF1. Although native forms of MGF are membrane bound and consist of an extracellular, transmembrane and cytoplasmic domains, the MGF used in the fusion proteins of the present invention preferably consists solely of its extracellular region or a fragment thereof including all four Cys residues of the extracellular domain and lacks a transmembrane region and intracellular domain. The extracellular region of MGF or fragment thereof is a soluble polypeptide which is capable of binding the gene product of the c-kit proto-oncogene. Both human and murine native sequence MGF have been found in two variations. One human variant is set forth in FIG. 42 of EP-A-0 423 980. The other variant has a 28 amino acid deletion (of amino acids 149-177) and is referred to as Δ28 hMGF.

Human MGF polypeptides have a 185 amino acid extracellular domain. This polypeptide has five glycosylation sites and four Cys residues, with $Cys^3$ binding to $Cys^{89}$ and $Cys^{43}$ binding to $Cys^{138}$. Δ28 hMGF retains all four Cys residues, but eliminates the fifth glycosylation site. Several amino acids can be removed from the C-terminus of hMGF extracellular domain, up to $Cys^{138}$, while retaining biological activity. Similarly, the first three N-terminal amino acids can be removed, up to $Cys^3$ of mature human MGF, while retaining biological activity. Therefore, a human MGF polypeptide having only 136 amino acid residues, but retaining all four Cys residues, retains significant biological activity compared to full length 185 amino acid form of hMGF or Δ28 hMGF. Δ28 hMGF has significant biological activity and is the preferred MGF fragment for use in fusion proteins comprising MGF and IL-3.

Various other analogs of the hMGF molecule have been shown to retain MGF biological activity. For example, $Lys^{91}$ confers human species specificity to MGF and $Glu^{91}$ confers murine species specificity. Glycosylation sites can be altered to facilitate expression in yeast or mammalian cell systems. The region surrounding $Cys^{89}$ is important for receptor binding. However, the $Val^{90}$ can be substituted with any other amino acid without affecting biological activity. Human MGF analogs can vary in length from about 135 amino acids to about 185 amino acids constituting the extracellular domain of the hMGF polypeptide. Biologically active hMGF analog polypeptides comprise four Cys residues, but can vary at other positions according to the following sequence:

|     |     |     |     | $X_n$ | $X_n$ | $X_n$ | Cys | Arg | Asn | Arg | Val | Thr | Asn | Asn |
| --- | --- | --- | --- | --- | --- | --- | --- | --- | --- | --- | --- | --- | --- | --- |
| Val | Lys | Asp | Val | Thr | Lys | Leu | Val | Ala | Asn | Leu | Pro | Lys | Asp | Tyr |
| Met | Ile | Thr | Leu | Lys | Tyr | Val | Pro | Gly | Met | Asp | Val | Leu | Pro | Ser |
| His | Cys | Trp | Ile | Ser | Glu | Met | Val | Val | Gln | Leu | Ser | Asp | Ser | Leu |
| Thr | Asp | Leu | Leu | Asp | Lys | Phe | Ser | Asn | Ile | Ser | Glu | Gly | Leu | Ser |
| Asn | Tyr | Ser | Ile | Ile | Asp | Lys | Leu | Val | Asn | Ile | Val | Asp | Asp | Leu |
| Val | $R_1$ | Cys | $R_2$ | Q | Glu | Asn | Ser | Ser | Lys | Asp | Leu | Lys | Lys | Ser |
| Phe | Lys | Ser | Pro | Glu | Pro | Arg | Leu | Phe | Thr | Pro | Glu | Glu | Phe | Phe |
| Arg | Ile | Phe | Asn | Arg | Ser | Ile | Asp | Ala | Phe | Lys | Asp | Phe | Val | Val |
| Ala | Ser | Glu | Thr | Ser | Asp | Cys | $X_n$ | $X_n$ | $X_n$ | $X_n$ | $X_n$ | $X_n$ | $X_n$ | $X_n$ |
| $X_n$ | $X_n$ |     |     |     |     |     |     |     |     |     |     |     |     |     | wherein n is 0 or 1, X is any naturally occurring amino acid; $R_1$ is any amino acid except Glu; $R_2$ is any amino acid except Val; and Q is Lys or Arg to provide human specificity, or is Glu to provide murine specificity. Such MGF proteins may be use to provide the MGF domains of the fusion proteins of the present invention.

INTERLEUKIN-3

The term "IL-3" refers to proteins having substantially the same characteristics of IL-3 in that they are capable of binding to receptors for IL-3 or transducing a biological signal initiated by binding to IL-3 receptors, or cross-reacting with anti-IL-3 antibodies raised against IL-3. Such sequences are disclosed, for example, in EP Publ. Nos. 275,598 and 282,185. The term "IL-3" specifically includes analogs or subunits of native mammalian IL-3 polypeptides with substantially identical or substantially similar amino acid polypeptide sequences which exhibit at least some biological activity in common with native IL-3. Exemplary analogs of IL-3 are also disclosed in EP Publ. No. 282,185. Particularly preferred forms of IL-3 which may be fused to MGF in accordance with the present invention include huIL-3[$Pro^8Asp^{15}Asp^{70}$], huIL-3[$Ser^8Asp^{15}Asp^{70}$], and huIL-3[$Ser^8$]. A DNA sequence encoding another IL-3 protein suitable for incorporation into fusion proteins as described herein is on deposit with ATCC under accession number ATCC 67747. Other forms of IL-3 may also be used to provide the IL-3 domain of the fusion proteins of the present invention.

FUSION PROTEINS COMPRISING MGF AND IL-3

As used herein, the term "fusion protein" refers to a C-terminal to N-terminal fusion of MGF and IL-3. The fusion proteins of the present invention include constructs in which the C-terminal portion of MGF is fused to the N-terminal portion of IL-3, and also constructs in which the C-terminal portion of IL-3 is fused to the N-terminal portion of MGF. MGF is linked to IL-3 in such a manner as to produce a single protein which retains the biological activity of MGF and IL-3. In preferred aspects, MGF is linked to IL-3 via a linker sequence Examples of fusion proteins comprising MGF and IL-3 are shown in the accompanying Sequence Listing. SEQ ID NO:1 shows the nucleotide sequence and corresponding amino acid sequence of a human IL-3/MGF fusion protein, referred to as PIXY521. The fusion protein comprises human IL-3 (amino acids 1–133) linked to human MGF (amino acids 145–301) via a linker sequence (amino acids 134–144). SEQ ID NO:3 shows a nucleotide sequence and corresponding amino acid sequence of a human MGF/IL-3 fusion protein. The fusion protein comprises human MGF (amino acids 1–157) linked to human IL-3 (amino acids 171–303) via a linker sequence (amino acids 158–170).

Equivalent fusion proteins may vary from the sequence of SEQ ID NO:1 and SEQ ID NO:3 by one or more substitutions, deletions, or additions, the net effect of which is to retain biological activity of the protein when derived as a fusion protein comprising MGF and IL-3. Alternatively, DNA analog sequences are equivalent to the specific DNA sequences disclosed herein if: (a) the DNA analog sequence comprises sequences derived from a biologically active fragments of the native IL-3 and MGF genes; or (b) the DNA analog sequence is capable of hybridization to DNA sequences of (a) under high or moderate stringent conditions and encodes biologically active MGF and IL-3 molecules; or (c) DNA analog sequence is degenerate as a result of the genetic code to the DNA analog sequences defined in (a) or (b) and which encode biologically active MGF and IL-3 molecules.

Moderate stringency hybridization conditions, as defined herein and as known to those of skill in the art, refer to conditions described in, for example, Sambrook et al. *Molecular Cloning: A Laboratory Manual*, 2 Ed. Vol. 1 pages 1.101–1.104 (Cold Spring Harbor Laboratory Press 1989). Exemplary conditions of moderate stringency are prewashing with 5×SSC, 0.5% SDS, 1 mM EDTA (pH 8.0) and overnight hybridization at 50° C. in 2×SSC. Exemplary severe or high stringency conditions are overnight hybridization at about 68° C. in a 6×SSC solution, washing at room temperature with 6×SSC solution, followed by washing at about 68° C. in a 0.6×SSC solution.

CONSTRUCTION OF CDNA SEQUENCES ENCODING FUSION PROTEINS COMPRISING MGF AND IL-3

A DNA sequence encoding a fusion protein is constructed using recombinant DNA techniques to assemble separate DNA fragments encoding MGF and IL-3 into an appropriate expression vector. For example, the 3' end of a DNA fragment encoding MGF is ligated to the 5' end of the DNA fragment encoding IL-3, with the reading frames of the sequences in phase to permit mRNA translation of the sequences into a single biologically active fusion protein. The resulting protein is fusion protein comprising MGF and IL-3. Alternatively, the 3′ end of a DNA fragment encoding IL-3 may be ligated to the 5′ end of the DNA fragment encoding MGF, with the reading frames of the sequences in phase to permit mRNA translation of the sequences into a single biologically active fusion protein. The regulatory elements responsible for transcription of DNA into mRNA are retained on the first of the two DNA sequences, while binding signals or stop codons, which would prevent read-through to the second DNA sequence, are eliminated. Conversely, regulatory elements are removed from the second DNA sequence while stop codons required to end translation are retained.

In preferred aspects of the present invention, means are provided for linking the MGF and IL-3 domains, preferably via a linker sequence. The linker sequence separates MGF and IL-3 domains by a distance sufficient to ensure that each domain properly folds into its secondary and tertiary structures. Suitable linker sequences (1) may adopt a flexible or a more rigid, extended conformation, (2) will not exhibit a propensity for developing an ordered secondary structure which could interact with the functional MGF and IL-3 domains, and (3) will have minimal hydrophobic or charged character which could promote interaction with the functional protein domains. Typical surface amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, may also be used in the linker sequence.

The length of the linker sequence may vary without significantly affecting the biological activity of the fusion protein. For example, the MGF and IL-3 proteins may be directly fused without a linker sequence. Linker sequences are unnecessary where the proteins being fused have non-essential N- or C-terminal amino acid regions which can be used to separate the functional domains and prevent steric interference. In one preferred embodiment of the present invention, the C-terminus of MGF may be directly fused to the N-terminus of IL-2. Full-length hMGF has 47 and Δ28 hMGF has 19 amino acids following the C-terminal cysteine residue in the extracellular region, which is involved in disulfide bonding and is essential for proper folding of the protein. IL-3 has 15 amino acids preceding its N-terminal cysteine residue. The combined terminal regions may therefore provide sufficient separation to render the use of a linker sequence unnecessary.

Generally, the two protein domains will be separated by a distance approximately equal to the small unit dimension of MGF or IL-3 (i.e., approximately 0.38 nm, as determined by analogy with other similar four-helix hormones). In a preferred aspect of the invention, a linker sequence length of about 11 amino acids is used to provide a suitable separation of functional protein domains, although longer linker sequences may also be used. The length of the linker sequence separating MGF and IL-3 is from 1 to 500 amino acids in length, or more preferably from 1 to 100 amino acids in length. In the most preferred aspects of the present invention, the linker sequence is from about 1–20 amino acids in length. In the specific embodiments disclosed herein, the linker sequence is from about 5 to about 15 amino acids, and is advantageously from about 10 to about 15 amino acids. Preferred amino acid sequences for use as linkers of MGF and IL-3 include, for example, GlyAla-GlyGlyAlaGlySer(Gly)$_5$Ser, (Gly$_4$Ser)$_3$Gly$_4$Ser-Gly$_5$Ser, (Gly$_4$Ser)$_2$, and (GlyThrPro)$_3$.

The linker sequence is incorporated into the fusion protein construct by well known standard methods of mutagenesis as described below.

PROTEINS AND ANALOGS

In preferred aspects, the present invention provides a fusion protein comprising human MGF and human IL-3. Derivatives of the fusion proteins of the present invention also include various structural forms of the primary protein which retain biological activity. Due to the presence of ionizable amino and carboxyl groups, for example, a fusion protein may be in the form of acidic or basic salts, or may be in neutral form. Individual amino acid residues may also be modified by oxidation or reduction.

The primary amino acid structure may be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups to amino acid side chains or at the N- or C-termini. Other derivatives of the fusion protein within the scope of this invention include covalent or aggregative conjugates of the fusion protein with other proteins or polypeptides, such as by synthesis in recombinant culture as N- or C-terminal fusions. For example, the conjugated peptide may be a signal (or leader) polypeptide sequence at the N-terminal region of the protein which co-translationally or postotranslationally directs transfer of the protein from its site of synthesis to its site of function inside or outside of the cell membrane or wall (e.g., the yeast α-factor leader).

Peptides may also be added to facilitate purification or identification of MGF/IL-3 fusion proteins (e.g., poly-His). For example, in a preferred embodiment of the present invention, the amino acid sequence of the fusion protein is linked to the peptide Asp-Tyr-Lys-Asp-Asp-Asp-Asp-Lys (DYKDDDDK) (Hopp et al., *Bio/Technology* 6:1204, 1988). The latter sequence is highly antigenic and provides an epitope reversibly bound by a specific monoclonal antibody, enabling rapid assay and facile purification of expressed recombinant protein. This sequence is also specifically cleaved by bovine mucosal enterokinase at the residue immediately following the Asp-Lys pairing. Fusion proteins capped with this peptide may also be resistant to intracellular degradation in *E. coli.*

Fusion protein derivatives may also be used as immunogens, reagents in receptor-based immunoassays, or as binding agents for affinity purification procedures of binding ligands. Derivatives may also be obtained by cross-linking agents, such as M-maleimidobenzoyl succinimide ester and N-hydroxysuccinimide, at cysteine and lysine residues. Fusion proteins may also be covalently bound through reactive side groups to various insoluble substrates, such as cyanogen bromide-activated, bisoxirane-activated, carbonyldiimidazole-activated or tosyl-activated agarose structures, or by adsorbing to polyolefin surfaces (with or without glutaraldehyde cross-linking).

The present invention also includes proteins with or without associated native-pattern glycosylation. Expression of DNAs encoding the fusion proteins in bacteria such as *E. coli* provides non-glycosylated molecules. Functional mutant analogs having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-A$_1$-Z, where A$_1$ is any amino acid except Pro, and Z is Ser or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between A$_1$ and Z, or an amino acid other than Asn between Asn and A$_1$. Human MGF has three possible glycosylation sites at amino acids 209–211, 216–218, 237–239 and 264–266 (SEQ ID NO:1) which may be removed. Examples of human IL-3 analogs in which glycosylation sites have been removed include huIL-3[Pro$^8$Asp$^{15}$Asp$^{70}$], huIL-3[Asp$^{70}$], huIL-3[Asp$^{15}$Asp$^{70}$], huIL-3[Pro$^8$Asp$^{15}$], huIL-3[Pro$^8$Asp$^{70}$], and huIL-3[Asp$^{15}$](SEQ ID NO:1).

Derivatives and analogs may also be obtained by mutations of the fusion protein. A derivative or analog, as referred to herein, is a polypeptide in which the MGF and IL-3 domains are substantially homologous to the extracellular region of MGF and the full-length IL-3 of the sequences disclosed in SEQ ID NO:1 but which has an amino acid sequence difference attributable to a deletion, insertion or substitution.

Bioequivalent analogs of fusion proteins may be constructed by, for example, making various substitutions of residues or sequences. For example, cysteine residues can be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present. Generally, substitutions should be made conservatively; i.e., the most preferred substitute amino acids are those having physicochemical characteristics resembling those of the residue to be replaced. Similarly, when a deletion or insertion strategy is adopted, the potential effect of the deletion or insertion on biological activity should be considered.

Mutations in nucleotide sequences constructed for expression of analogs must, of course, preserve the reading frame phase of the coding sequences and preferably will not create complementary regions that could hybridize to produce secondary mRNA structures such as loops or hairpins which would adversely affect translation of the MGF/IL-3 receptor mRNA. Although a mutation site may be predetermined, it is not necessary that the nature of the mutation per se be predetermined. For example, in order to select for optimum characteristics of mutants at a given site, random mutagenesis may be conducted at the target codon and the expressed mutants screened for the desired activity.

Not all mutations in nucleotide sequences which encode fusion proteins comprising MGF and IL-3 will be expressed in the final product, for example, nucleotide substitutions may be made to enhance expression, primarily to avoid secondary structure loops in the transcribed mRNA (see EPA 75,444A, incorporated herein by reference), or to provide codons that are more readily translated by the selected host, e.g., the well-known *E. coli* preference codons for *E. coli* expression.

Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, January 1985, 12-19); Smith et al. (*Genetic Engineering: Principles and Methods*, Plenum Press, 1981); and U.S. Pat. Nos. 4,518,584 and 4,737,462, and are incorporated by reference herein.

EXPRESSION OF RECOMBINANT FUSION PROTEINS COMPRISING MGF AND IL-3

The present invention provides recombinant expression vectors which include synthetic or cDNA-derived DNA fragments encoding human fusion proteins comprising MGF and IL-3 or bioequivalent analogs operably linked to suitable transcriptional or translational regulatory elements derived from mammalian, microbial, viral or insect genes. Such regulatory elements include a transcriptional promoter, an optional operator sequence to control transcription, a sequence encoding suitable mRNA ribosomal binding sites, and sequences which control the termination of transcription and translation, as described in detail below. The ability to replicate in a host, usually conferred by an origin of replication, and a selection gene to facilitate recognition of transformants may additionally be incorporated. DNA regions are operably linked when they are functionally contiguous to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame.

Due to code degeneracy, there can be considerable variation in nucleotide sequences encoding the same MGF or IL-3 amino acid sequence; exemplary DNA embodiments are those corresponding to the nucleotide sequences shown in SEQ ID NO:1 or SEQ ID NO:3. Other embodiments within the scope of the present invention include nucleotide sequences which encode fusion proteins comprising MGF and IL-3, in which the MGF and IL-3 encoding regions are capable of hybridizing to the respective MGF and IL-3 nucleotide regions of SEQ ID NO:1 or SEQ ID NO:3 under moderate or high stringency conditions and which encode biologically active fusion proteins.

Transformed host cells are cells which have been transformed or transfected with fusion protein vectors constructed using recombinant DNA techniques. Transformed host cells ordinarily express the desired fusion protein, but host cells transformed for purposes of cloning or amplifying DNA do not need to express the protein. Expressed fusion protein will generally be secreted into the culture supernatant. Suitable host cells for expression of fusion protein include prokaryotes, yeast or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed to produce fusion protein using RNAs derived from the DNA constructs of the present invention. Appropriate cloning and expression vectors for use with bacterial, fungal, yeast, and mammalian cellular hosts are described by Pouwels et al. (*Cloning Vectors: A Laboratory Manual*, Elsevier, N.Y., 1985), the relevant disclosure of which is hereby incorporated by reference.

Prokaryotic expression hosts may be used for expression of fusion protein that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium*, and various species within the genera Pseudomonas, Streptomyces, and Staphyolococcus, although others may also be employed as a matter of choice.

Useful expression vectors for bacterial use can comprise a selectable marker and bacterial origin of replication derived from commercially available plasmids comprising genetic elements of the well-known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2:95, 1977). pBR322 contains genes for ampicillin and tetracycline resistance and thus provides simple means for identifying transformed cells.

Promoters commonly used in recombinant microbial expression vectors include the β-lactamase (penicillinase) and lactose promoter system (Chang et al., *Nature* 275:6 15, 1978; and Goeddel et al., *Nature* 281:544, 1979), the tryptophan (trp) promoter system (Goeddel et al., *Nucl. Acids Res.* 8:4057, 1980; and EPA 36,776) and tac promoter (Maniatis, *Molecular Cloning: A Laboratory Manual*, Cold Spring Harbor Laboratory, p. 412, 1982). A particularly useful bacterial expression system employs the phage $\lambda P_L$ promoter and cI857ts thermoinducible repressor. Plasmid vectors available from the American Type Culture Collection which incorporate derivatives of the $\lambda P_L$ promoter include plasmid pHUB2, resident in *E. coli* strain JMB9 (ATCC 37092) and pPLc28, resident in *E. coli* RR1 (ATCC 53082).

Recombinant fusion proteins may also be expressed in yeast hosts, preferably from the Saccharomyces species, such as *S. cerevisiae*. Yeast of other genera such as Pichia or Kluyveromyces may also be employed. Yeast vectors will generally contain an origin of replication from the 2μ yeast plasmid or an autonomously replicating sequence (ARS), promoter, DNA encoding the fusion protein, sequences for polyadenylation and transcription termination and a selection gene. Preferably, yeast vectors will include an origin of replication and selectable marker permitting transformation of both yeast and *E. coli*, e.g., the ampicillin resistance gene of *E. coli* and *S. cerevisiae* trp 1 gene, which provides a selection marker for a mutant strain of yeast lacking the ability to grow in tryptophan, and a promoter derived from a highly expressed yeast gene to induce transcription of a structural sequence downstream. The presence of the trp 1 lesion in the yeast host cell genome then provides an effective environment for detecting transformation by growth in the absence of tryptophan.

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EP-A-0 073 657.

Preferred yeast vectors can be assembled using DNA sequences from pBR322 for selection and replication in *E. coli* (Amp$^r$ gene and origin of replication) and yeast DNA sequences including a glucose-repressible ADH2 promoter and α-factor secretion leader. The ADH2 promoter has been described by Russell et al. (*J. Biol. Chem.* 258:2674, 1982) and Beier et al. (*Nature* 300:724, 1982). The yeast α-factor leader, which directs secretion of heterologous proteins, can be inserted between the promoter and the structural gene to be expressed. See, e.g., Kurjan et al., *Cell* 30:933, 1982; and Bitter et al., *Proc. Natl. Acad. Sci. USA* 81:5330, 1984. The leader sequence may be modified to contain, near its 3' end, one or more useful restriction sites to facilitate fusion of the leader sequence to foreign genes. Exemplary yeast expression vectors are PIXY521 and PIXY523, described in Examples 1 and 2 below.

Suitable yeast transformation protocols are known to those of skill in the art; an exemplary technique is described by Hinnen et al., *Proc. Natl. Acad. Sci. USA* 75: 1929, 1978, selecting for Trp+ transformants in a selective medium consisting of 0.67% yeast nitrogen base, 0.5% casamino acids, 2% glucose, 10 μg/ml adenine and 20 μg/ml uracil.

Host strains transformed by vectors comprising the ADH2 promoter may be grown for expression in a rich nutrient medium consisting of 1% yeast extract, 2% peptone, and 1% glucose supplemented with 80 μg/ml adenine and 80 μg/ml uracil. Derepression of the ADH2 promoter occurs upon exhaustion of medium glucose. Crude yeast supernatants are collected by filtration or centrifugation and held at 4° C. prior to further purification. In the most preferred embodiments of the present invention, the yeast host cells are cultured in a high cell density fermentation process in which the nutrient medium is added at a continuous rate during fermentation to permit high cell density growth. An exemplary high cell density fermentation process is described below in Example 3.

Various mammalian or insect cell culture systems can be employed to express recombinant protein. Baculovirus systems for production of heterologous proteins in insect cells are reviewed by Luckow and Summers, *Bio/Technology* 6:47 (1988). Examples of suitable mammalian host cell lines include the COS-7 lines of monkey kidney cells, described by Gluzman (*Cell* 23:175, 1981), and other cell lines capable of expressing an appropriate vector including, for example, L cells, C127, 3T3, Chinese hamster ovary (CHO), HeLa and BHK cell lines. Mammalian expression vectors may comprise non-transcribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a poly-adenylation site, splice donor and acceptor sites, and transcriptional termination sequences.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273:113, 1978). Smaller or larger SV40 fragments may also be used, provided the approximately 250 bp sequence extending from the Hind III site toward the BglI site located in the viral origin of replication is included. Exemplary vectors can be constructed as disclosed by Okayama and Berg (*Mol. Cell. Biol.* 3:280, 1983).

A useful system for stable high level expression of mammalian receptor cDNAs in C127 murine mammary epithelial cells can be constructed substantially as described by Cosman et al. (*Mol. Immunol.* 23:935, 1986).

Particularly preferred eukaryotic vectors for expression of MGF/IL-3 DNA include pIXY521 and pIXY523, both of which are yeast expression vectors derived from pBC102.K22 (ATCC 67,255) and contain DNA sequences from pBR322 for selection and replication in *E. coli* (Apr gene and origin of replication) and yeast, as described below in Examples 1 and 2.

Purified mammalian fusion proteins or analogs are prepared by culturing suitable host/vector systems to express the recombinant translation products of the DNAs of the present invention, which are then purified from culture media or cell extracts.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. For example, a suitable affinity matrix can comprise a MGF or IL-3 receptor or leetin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred.

Finally, one or more reversed-phase high performance liquid chromatography (RP-HPLC) steps employing hydrophobic RP-HPLC media, e.g., silica gel having pendant methyl or other aliphatic groups, can be employed to further purify a fusion protein composition. Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant fusion proteins can be disrupted by any convenient method, including freeze-thaw cycling, sonication, mechanical disruption, or use of cell lysing agents.

Fermentation of yeast which express fusion proteins as a secreted protein greatly simplifies purification. Secreted recombinant protein resulting from a large-scale fermentation can be purified by methods analogous to those disclosed by Urdal et al. (*J. Chromatog.* 296:171, 1984). This reference describes two sequential, reversed-phase HPLC steps for purification of recombinant murine GM-CSF on a preparative HPLC column.

Fusion protein synthesized in recombinant culture is characterized by the presence of non-human cell components, including proteins, in amounts and of a character which depend upon the purification steps taken to recover the fusion protein from the culture. These components ordinarily will be of yeast, prokaryotic or non-human higher eukaryotic origin and preferably are present in innocuous contaminant quantities, on the order of less than about 5 percent by scanning densitometry or chromatography. Further, recombinant cell culture enables the production of the fusion protein free of proteins which may be normally associated with MGF or IL-3 as they are found in nature in their respective species of origin, e.g., in cells, cell exudates or body fluids.

Fusion protein compositions are prepared for administration by mixing fusion protein having the desired degree of purity with physiologically acceptable carders. Such careers will be nontoxic to recipients at the dosages and concentrations employed. Ordinarily, the preparation of such compositions entails combining the fusion protein with buffers, antioxidants such as ascorbic acid, low molecular weight (less than about ten residues) polypeptides, proteins, amino acids, carbohydrates including glucose, sucrose or dextrins, chelating agents such as EDTA, glutathione and other stabilizers and excipients.

Fusion protein compositions may be used to enhance proliferation, differentiation and functional activation of hematopoietic progenitor cells, such as bone marrow cells. Specifically, compositions containing the fusion protein may be used to increase peripheral blood leukocyte numbers and increase circulating granulocyte counts in myelosuppressed patients. To achieve this result, a therapeutically effective quantity of a fusion protein composition is administered to a mammal, preferably a human, in association with a pharmaceutical carder or diluent.

The following examples are offered by way of illustration, and not by way of limitation.

EXAMPLES

Example 1

Synthesis of Expression Vectors Encoding an MGF/IL-3 Fusion Protein

A. Construction of PIXY321 Intermediate Plasmid. Peripheral blood lymphocytes were isolated from buffy coats prepared from whole blood (Portland Red Cross, Portland, Oreg., USA) by Ficoll hypaque density centrifugation. T cells were isolated by rosetting with 2-amino-ethylthiouronium bromide-treated sheep red blood cells. Cells were cultured in 175 cm$^2$ flasks at $5 \times 10^6$ cells/ml for 18 hour in 100 ml RPMI, 10% fetal calf serum, 50 μM b-mercaptoethanol, 1% phytohemagglutinin (PHA) and 10 ng/ml phorbol 12-myristate 13-acetate (PMA). RNA was extracted by the guanidinium CsCl method and poly A+ RNA prepared by oligo-dT cellulose chromatography (Maniatis et al., *Molecular Cloning: A Laboratory Manual,* Cold Spring Harbor, 1982). cDNA was prepared from poly A+ RNA essentially as described by Gubler and Hoffman, *Gene* 25:263–269 (1983). The cDNA was rendered double-stranded using DNA polymerase I, blunt-ended with T4 DNA polymerase, methylated with EcoR1 methylase to protect EcoR1 cleavage sites within the cDNA, and ligated to EcoR1 linkers. These constructs were digested with EcoR1 to remove all but one copy of the linkers at each end of the cDNA, ligated to EcoR 1-cut and dephosphorylated arms of phage λgt10 (Huynh et al., *DNA Cloning: A Practical Approach,* Glover, ed., IRL Press, pp. 49–78) and packaged into λ phage extracts (Stratagene, San Diego, Calif., USA) according to the manufacturer's instructions. 500,000 recombinants were plated on *E. coli* strain C600hfl- and screened by standard plaque hybridization techniques using the following probes.

Two oligonucleotides were synthesized, with sequences complementary to selected 5' and 3' sequences of the huIL-3 gene. The 5' probe, complementary to a sequence encoding part of the huIL-3 leader, had the sequence 5'-GAGTTGGAGCAGGAGCAGGAC-3'. The 3' probe, corresponding to a region encoding amino acids 123–130 of the mature protein, had the sequence 5'-GATCGCGAGGCTCAAAGTCGT-3'. The method of synthesis was a standard automated triester method substantially similar to that disclosed by Sood et at., *Nucl. Acids Res.* 4:2557 (1977) and Hirose et al., *Tet. Lett.* 28:2449 (1978). Following synthesis, oligonucleotides were deblocked and purified by preparative gel electrophoresis. For use as screening probes, the oligonucleotides were terminally radiolabeled with $^{32}$P-ATP and T4 polynucleotide kinase using techniques similar to those disclosed by Maniatis et al. The *E. coli* strain used for library screening was C600hfl- (Huynh et al., 1985, supra).

Thirteen positive plaques were purified and reprobed separately with the two hybridization probes. Eleven clones hybridized to both oligonucleotides. The cDNA inserts from several positive recombinant phage were subcloned into an EcoR1-cut derivative (pGEMBL18) of the standard cloning vector pBR322 containing a polylinker having a unique EcoR1 site, a BamH1 site and numerous other unique restriction sites. An exemplary vector of this type, pGEMBL, is described by Dente et al., *Nucl. Acids Res.* 11:1645 (1983), in which the promoters for SP6 and T7 polymerases flank the multiple cloning sites. The nucleotide sequences of selected clones were determined by the chain termination method. Specifically, partial EcoR1 digestion of λGT10:IL-3 clones 2, 3, 4 and 5 yielded fragments ranging from 850 bp to 1,000 bp in size which were separately subcloned into the EcoR1 site of pGEMBL18. The inserts of the pGEMBL:rhuIL-3 subclones were sequenced using a universal primer that binds adjacent to the multiple cloning site of pGEMBL18, and synthetic oligonucleotide primers derived from the huIL-3 sequence.

The two asparagine-linked glycosylation sites present in the natural protein (Asn[15] and Asn[70]) were altered by changing the codons at these positions to ones that encode aspartic acid. This prevents N-linked glycosylation (often hyperglycosylation) of the secreted protein by the yeast cells, and a more homogeneous product is obtained. These changes were made as described below upon subcloning the huIL-3 cDNA into the yeast expression vector pIXY120.

The yeast expression vector pIXY120 is substantially identical to pBC102-K22, described in EPA 243,153, except that the following synthetic oligonucleotide containing multiple cloning sites was inserted from the Asp718 site (amino acid 79) near the 3' end of the α-factor signal peptide to the SpeI site contained in the 2μ sequences:

in oligonucleotide A represent changes from the wild type cDNA sequence. Only the A to G and C to T changes at nucleotides 43 and 45, respectively (counting from the codon corresponding to the N-terminal alanine of the mature huIL-3 molecule), result in an amino acid change (Asp[15]). The other base changes introduce convenient restriction sites (AhaII and PvuII) without altering the amino acid sequence. The resulting plasmid was designated pIXY 139 and contains a rhuIL-3 cDNA with one remaining N-linked glycosylation consensus sequence (Asn[70]).

Plasmid pIXY 139 was used to perform oligonucleotide-directed mutagenesis to remove the second N-linked glycosylation consensus sequence by changing Asn[70] to Asp[70]. The in vitro mutagenesis was conducted by a method similar to that described by Walder and Walder, Gene 42:133 (1986). The yeast vector, pIXY139, contains the origin of replication for the single-stranded bacteriophage f1 and is capable of generating single-stranded DNA when present in a suitable (male) strain of E. coli and superinfected with helper phage.

Single-stranded DNA was generated by transforming E. coli strain JM107 and superinfecting with helper phage IR1. Single-stranded DNA was isolated and annealed to the following mutagenic oligonucleotide B, GTC AAG AGT TTA CAG GAC GCA TCA GCA

```
Asp718                                                          /NcoI
GTACCTTTGGATAAAAGAGACTACAAGGACGACGATGACAAGAGGCCTCCATGGATCCCCCGGGACA
     GAAACCTATTTTCTCTGATGTTCCTGCTGCTACTGTTCTCCGGAGGTACCTAGGGGGCCCTGTGATC
                                                   /BamH1      SpeI
```

In addition, a 514-bp DNA fragment derived from the single-stranded bacteriophage f1 containing the origin of replication and intergenic region was inserted at the NruI site in the pBR322 DNA sequences. The presence of the f1 origin of replication enables generation of single-stranded copies of the vector when transformed into appropriate (male) strains of E. coli and superinfected with bacteriophage $f_1$. This capability facilitates DNA sequencing of the vector and allows the possibility of in vitro mutagenesis.

The yeast expression vector pIXY120 was digested with the restriction enzymes Asp718, which cleaves near the 3' end of the α-factor leader peptide (nucleotide 237), and BamH1, which cleaves in the polylinker. The large vector fragment was purified and ligated to the following DNA fragments: (1) a huIL-3 cDNA fragment derived from plasmid GEMBL18:huIL-3 from the ClaI site (nucleotide 58 of mature huIL-3) to the BamH1 site (3' to the huIL-3 cDNA in a polylinker); and (2) the following synthetic oligonucleotide linker A:

AAT G, which provides a codon switch substituting Asp for Asn at position 70 of mature huIL-3. Annealing and yeast transformation conditions were done as described by Walder and Walder, supra. Yeast transformants were selected by growth on medium lacking tryptophan, pooled, and DNA extracted as described by Holm et al., Gene 42:169 (1986). This DNA, containing a mixture of wild type and mutant plasmid DNA, was used to transform E. coli RR1 to ampicillin resistance. The resulting colonies were screened by hybridization to radiolabeled oligonucleotide B using standard techniques. Plasmids comprising DNA encoding huIL-3 Asp[70] were identified by the hybridization to radiolabeled oligonucleotide B under stringent conditions and verified by nucleotide sequencing.

The resulting yeast expression plasmid was designated pIXY138, and contained the huIL-3 gene encoding the Asp[15] Asp[70] amino acid changes and the octapeptide DYKDDDDK at the N-terminus. The final yeast expression plasmid is identical to pIXY138 except that it lacks the nucleotide sequences coding for the

```
GTA CCT TTG GAT AAA AGA GAC TAC AAG GAC GAC GAT GAC AAG GCT CCC ATG ACC CAG
    GA AAC CTA TTT TCT GTG ATG TTC CTG CTG CTA CTG TTC CGA GGG TAC TGG GTC

ACG ACG CCC TTG AAG ACC AGC TGG GTT GAT TGC TCT AAC ATG AT
TGC TGC GGG AAC TTC TGG TCG ACC CAA CTA ACG AGA TTG TAC TAG C
```

Oligonucleotide A regenerates the sequence encoding the C-terminus of the α-factor leader peptide and fusing it in-frame to the octapeptide DYKDDDDK, which is, in turn, fused to the N-terminus of mature rhuIL-3. This fusion to the rhuIL-3 protein allows detection with antibody specific for the octapeptide and was used initially for monitoring the expression and purification of rhuIL-3. This oligonucleotide also encodes an amino acid change at position 15 (Asn[15] to Asp[15]) to alter this N-linked glycosylation site. The underlined nucleotides octapeptide, thus generating mature rhuIL-3 as the product.

The final yeast expression plasmid encoding IL-3 was constructed as described below. The yeast expression vector pIXY120 was cleaved with the restriction enzymes Asp718 and BamH1 as described above. The large vector fragment was ligated together with (1) a huIL-3 cDNA fragment derived from plasmid pIXY138 that extended from the Aha2 site (which cleaves at nucleotide 19 of mature huIL-3) to the BamH1 site 3' to the cDNA, and (2) the following synthetic oligonucleotide C:

```
      GTA CCT TTG GAT AAA AGA GCT CCC ATG ACC CAG ACG A
         GA AAC CTA TTT TCT CGT GGG TAC TGG GTC TGC TGC
         Pro Leu Asp Lys Arg Ala Pro Met Thr Gln Thr Thr
```

Oligonucleotide C regenerates the 3' end of the a-factor leader peptide from the Asp718 site (the amino acids Pro-Leu-Asp-Lys-Arg) and the N-terminal seven amino acids of huIL-3 to the AhaII site. The resulting plasmid was designated pIXY151. This vector, when present in yeast, allows glucose-regulated expression and secretion of rhuIL-3 (Pro$^8$ Asp$^{15}$ Asp$^{70}$).

The plasmid PIXY321 (encoding a GM-CSF/IL-3 fusion protein) was constructed as follows and used as an intermediate in constructing the MGF/IL-3 fusion protein. The wild-type gene coding for human GM-CSF, resident on plasmid priG23, has been deposited with the American Type Culture Collection (ATCC), 12301 Parklawn Drive, Rockville, Md. 20852, USA, under accession number 39900. The wild-type gene inserted in a yeast expression vector, pYafHuGM, has also been deposited with the ATCC under accession number 53157. In order to provide a non-glycosylated analog of human GM-CSF, oligonucleotide-directed site-specific mutagenesis procedures were employed to eliminate potential N-glycosylation sites, as described in PCT publication WO 89/03881. A plasmid encoding this analog, huGM-CSF (Leu$^{23}$ Asp$^{27}$ Glu$^{39}$), was deposited with the ATCC as plasmid L207-3 in E. coli strain RR1 under accession number 67231.

DNAs encoding GM-CSF and IL-3 were first ligated together without regard to reading frame or intervening sequences. A cDNA fragment encoding non-glycosylated human GM-CSF was excised from plasmid L207-3 as a 977bp restriction fragment (Sph1 to Ssp1). The IL-3 cDNA was excised from pIXY151 by digestion with Asp718, which was then blunt ended using the T4 polymerase reaction of Maniatas et al. (*Molecular Cloning: A Laboratory Manual,* Cold Spring Harbor, 1982, p. 118) and further digested with XhoI giving an 803 bp fragment. These two fragments were then directly ligated to a pIXY151 vector fragment cut with Sph1 and Xho1. This plasmid was called GM/IL-3 direct fusion.

The GM/IL-3 direct fusion plasmid was used as a template in oligonucleotide-directed mutagenesis using methods similar to those described by Walder and Walder, supra. The following oligonucleotide was then synthesized (Stratagene) and the methods of Russel et al. (*Gene* 45:333–338, 1986). Oligonucleotide directed mutagenesis was then carried out by annealing the above oligonucleotide to the single stranded plasmid DNA and transforming yeast strain XV2181 with annealed DNA as described by Walder and Walder, supra. The yeast vector contains the origin of replication for the single stranded bacteriophage f$_1$ and is capable of sponsoring single stranded DNA production when present in a suitable (male) strain of E. coli and superinfected with helper phage. Yeast transformants were selected by growth on medium lacking tryptophan, pooled, and DNA was extracted as described by Holm et at. (*Gene* 42:169, 1986). This DNA, containing a mixture of mutant and wild type plasmid DNA, was used to transform E. coli RR1 to ampicillin resistance. The resulting colonies were screened by hybridization to radiolabeled oligonucleotide using standard techniques. Plasmids comprising DNA encoding GM-CSF/linker/IL-3 were identified by their hybridization to radiolabeled oligonucleotide containing the linker under stringent conditions and verified by nucleotide sequencing.

During nucleotide sequencing it was discovered that a mutation had occurred within the linker region. The nucleotide sequence TGGTGGATCTGG was deleted (see sequence), resulting in the expression of a protein in which the sequence of amino acids GlyGlySerGly were deleted. This mutation did not change the reading frame or prevent expression of a biologically active protein. The resulting plasmid was designated pIXY321 and expressed the fusion protein huGM-CSF[Leu$^{23}$Asp$^{27}$Glu$^{39}$]/Gly$_4$SerGly$_5$Ser/huIL-3[Pro$^8$Asp$^{15}$Asp$^{70}$]. This plasmid was use as described below as an intermediate plasmid in constructing fusion proteins comprising MGF and IL-3.

B. Construction of Vector Encoding MGF. A yeast expression vector encoding MGF was constructed by inserting the huMGF-2D cDNA sequence into the pIXY-120 vector, described above. The huMGF-2D cDNA also contains the ADH2 promoter sequence, an factor leader sequence, and a sequence encoding a FLAG ® identification peptide (AspLysArgAspAspAspAspLys) contiguous and in reading frame with MGF to facilitate purification of the expressed protein. The resulting vector was designated pIXY490.

C. Construction of Vector Encoding Fusion Protein Comprising MGF and IL-3. A vector encoding a fusion protein comprising MGF and IL-3 was constructed by

```
GCCAGTCCAGGAGGGTGGCGGTGGATCCGGCGGTGGTGGATCTGGTGGCGGCGGCTCAGCTCCCATGACCC

Pro Val Gln GluGly Gly Gly Gly Ser Gly Gly Gly Gly Ser Gly Gly Gly Gly SerAla Pro Met Thr
 — GM—CSF —><——————————————————— Linker ——————————————————><—— IL—3 —
```

This oligonucleotide overlaps the 3' end of GM-CSF by 13 bp but does not include the stop codon, contains the Gly Ser linker, and overlaps the 5' end of IL-3 by 13 bp. The linker sequence was a modified version of the linker described by Huston et al. (*Proc. Natl. Acad. Sci. USA* 85:5879–5883, 1988) but was optimized for codon usage in yeast as per Bennetzen et al. (*J. Biol. Chem.* 257:3026, 1982).

Single stranded plasmid DNA was made from the GM/IL-3 direct fusion using R408 helper phage combining four cDNA fragments containing regulatory sequences for yeast expression, and DNA sequences encoding a FLAG ® identification peptide, MGF and IL-3. The first cDNA fragment contained the plasmid backbone and a portion of the ADH2 promoter and was excised from PIXY490 as a SpiH1 to BamH1 fragment.

The second fragment contained the remaining portion of the ADH2 promoter, the α-factor leader, sequences encoding the FLAG ® identification peptide (GACTACAAGGACGAC GATGACAAG) and the 5' end of the extracellular region of human MGF and was excised as a SpHI to EcoRI restfiction fragment of pIXY490, described above.

The third fragment contained sequences encoding the Y end of the extracellular region of human MGF. The linker sequence joining the MGF coding region and the IL-3 coding region was generated by polymerase chain reaction (PCR) using the following 5' PCR oligonucleotide primer which corresponds to the coding region of MGF (nucleotides 334–357 of SEQ ID NO:3) and includes an EcoRI restriction site:

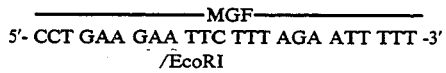
5'- CCT GAA GAA TTC TTT AGA ATT TTT -3'
/EcoRI and the following 3' PCR oligonucleotide antisense primer of which a portion is complementary to the 3' end of MGF (nucleotides 460–471 of SEQ ID NO:3) and introduces part of a linker sequence (nucleotides 472–492 of SEQ ID NO:3) containing SfiI and BamHI restriction sites contiguous to the 3' end of MGF:

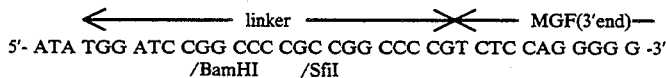
5'- ATA TGG ATC CGG CCC CGC CGG CCC CGT CTC CAG GGG G -3'
/BamHI    /SfiI Following synthesis, the oligonucleotides were deblocked and purified by preparative gel electrophoresis. For use as screening probes, the oligonucleotides were kinased with T4 polynucleotide kinase using techniques similar to those disclosed by Maniatis et al. A cDNA sequence encoding human MGF-2D which encodes the extracellular region of λ28 human MGF (amino acids 1–157, described in EP-A-0 423 980, FIG. 44) was subcloned into a pBluescript SK(-) cloning vector (Stratagene, La Jolla, Calif.). Using the resulting pBluescript-:huMGF2-D plasmid as a template, the above primers were used to amplify the 3' end of human MGF and to add the linker sequence joining human MGF and IL-3. Fifty pM of each primer and 50 ng template were combined in a reaction buffer containing 29.75 μl water, 5 μl 10x standard PCR buffer (500 mM KCl, 100 mM Tris-Cl (pH 8.3), 15 mM MgCl₂, 0.1% (w/v) gelatin), 5 μl 10X low magnesium buffer (500 mM KCl, 100 mM Tris-Cl (pH8.3), 5 mM MgCl₂, 0.1% gelatin) (for control) or 5 μl 10X low potassium buffer (50 mM KCl, 100 mM Tris-Cl, 15 mM MgCl₂, 0.1% gelatin), 8 μl 1.25 mM dNTPs, and 0.25 ml Taq polymerase. Reactions were performed on an Ericomp TwinBlock® temperature cycler (Ericomp, San Diego, Calif.) for 6 cycles of 94° C. for 30 seconds, 37° C. for 45 seconds and 72° C. for 30 seconds, followed by approximately 25 cycles of 94° C. for 30 seconds, 60° C. for 45 seconds and 72° C. for 30 seconds and an additional 5 minutes of extension at 72° C. Agarose gel electrophoresis of the products of PCR amplification showed a band corresponding to the 3' end of human MGF.

The fourth fragment contained sequences encoding IL-3 and part of the linker sequence and was excised as a BamHI restriction fragment from pIXY321, described above. This fragment was treated with calf intestinal alkaline phosphatase (Boehringer Mannheim) to remove 5' phosphates.

The four cDNA fragments described above were combined in a four-way ligation to generate the yeast expression vector pIXY523, which contains sequences encoding an N-terminal FLAG® identification peptide linked to a fusion protein comprising MGF and IL-3. The sequence of the MGF/IL-3 fusion protein (the N-terminal FLAG® identification peptide is not shown) is set forth SEQ ID NO:3.

Example 2

Construction of IL-3/MGF Fusion Protein

A fusion protein comprising IL-3 followed by MGF was constructed by combining fragments containing regulatory sequences for yeast expression and coding sequences for IL-3 and MGF. The first cDNA fragment was obtained by excising a Pst1 to SnaB1 restriction fragment from pIXY490. This fragment contained most of the 5' end of the extracellular region of human MGF.

The second fragment was obtained by excising a SnaB1 to BamH1 restriction fragment from the plasmid PIXY344 and contained sequences encoding IL-3 and a portion of the linker sequence. The intermediate plasmid PIXY344 encodes an IL-3/GM-CSF fusion protein was constructed as follows. The yeast expression vector pIXY120 (described in Example 1, above) was digested with the restriction enzymes Asp718, which cleaves near the 3' end of the α-factor leader peptide (nucleotide 237), and Nco1, which cleaves in the polylinker. The large vector fragment was purified and ligated to an approximately 500bp Asp718-Nco1 fragment (encoding GM-CSF(Leu²³Asp²⁷Glu³⁹)) from a partial digest of L207-3 (ATCC 67231), to yield pIXY273. A 9kb Asp718-Bgl2 fragment of piXY273 (still containing the GM-CSF(Leu²³Asp²⁷Glu³⁹)cDNA) was then ligated to an Asp718-Nru1 fragment encoding human IL-3 (Pro⁸Asp¹⁵Asp⁷⁰) from pIXY151 (described in Example 1B) and the following double stranded oligonucloetide:

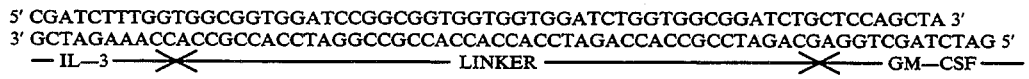
5' CGATCTTTGGTGGCGGTGGATCCGGCGGTGGTGGTGGATCTGGTGGCGGATCTGCTCCAGCTA 3'
3' GCTAGAAACCACCGCCACCTAGGCCGCCACCACCACCTAGACCACCGCCTAGACGAGGTCGATCTAG 5'
— IL—3 ——><—————— LINKER ——————><—— GM—CSF ——

This oligonucleotide overlaps the 3' end of IL-3 by 8bp but does not include the stop codon, contains the Gly-Ser linker, and overlaps the 5' end of GM-CSF by 10bp. The resulting vector was designated pIXY344 and contains sequences encoding an N-terminal IL-3 and a C-terminal GM-CSF.

The third fragment comprised the linker sequence and was generated by synthesizing, kinasing and annealing the following two oligonucleotides:

```
5'- GAT CCG GCG GTG GCG GCG GCT CAG AAG GGA TCT GCA -3'
3'-         GC CGC CAC CGC CGC CGA GTC TTC CCT AG        -5'
```

The three cDNA fragments described above were combined in a three-way ligation to generate the yeast expression vector pIXY521, which encodes a fusion protein comprising IL-3 and MGF. The sequence of this IL-3/MGF fusion protein is set forth SEQ ID NO:1.

Example 3

Expression and Purification of MGF/IL-3 Fusion Protein

The host strain, YNN281, a haploid *S. cerevisiae* strain [a, trpl-Δ, his3-Δ200, ura 3-52, lys 2-801$_a$, ade 2-1$_o$] was obtained from the Yeast Genetic Stock Center, University of California, Berkeley, Calif., USA. The host strain was transformed with the expression plasmid by the method of Sherman et al., *Laboratory Course Manual for Methods in Yeast Genetics*, Cold Spring Harbor Laboratory, 1986.

Yeast containing the expression plasmid PIXY523 (encoding the MGF/IL-3 fusion protein) was maintained on YNB-trp agar plates stored at 4° C. A preculture was started by inoculating several isolated recombinant yeast colonies into 50 ml of YNB-trp growth medium (Difco Laboratories, Detroit, Mich.) (6.7 g/L Yeast Nitrogen Base, 5 g/L casamino acids (Hy-Case SF ®), 40 mg/L adenine, 160 mg/L uracil, and 200 mg/L tyrosine) and was grown for 21 hours in a shake flask at 30° C. with vigorous shaking. By morning the culture was saturated, in stationary phase, at an OD$_{550}$ of 1.2.

The following reagents were prepared to the following concentrations: glucose (500 g/L), Hy-Case ® SF (Sheffield Products, Norwich, N.Y.) (60 g/L), yeast extract (Difco Laboratories, Detroit, Mich.) (200 g/L), peptone (Difco Laboratories, Detroit, Mich.) (200 g/L), yeast feed salts (250 g/L ammonium sulfate, 125 g/L monobasic potassium phosphate, anhydrous, 28.5 g/L magnesium sulfate), ethanol (95%), vitamins (0.02 g/L biotin, 2 g/L calcium pantothenate, 25 g/L myo-inositol, 5 g/L niacin, 0.4 g/L pyridoxine HCl, 0.1 g/L folic acid, 0.5 g/L choline chloride), trace elements (5 g/L boric acid, 2 g/L cupric sulfate, 10 g/L ferric chloride, 10 g/L manganese sulfate, 0.5 g/L sodium molybdate, 10 g/L, zinc sulfate, 0.5 g/L cobalt chloride), adenine (10 g/L), thiamine (10 g/L), uracil (10 g/L), histadine (10 g/L), lysine (15 g/L).

The growth medium for a 1 liter fermentation tank was prepared by combining 5.0 g potassium phosphate, 20.0 g ammonium sulfate, 1.0 g magnesium sulfate, 0.1 g calcium chloride, 0.2 ml L61 antifoam and water to a total volume of 650 ml. This medium was then sterilized by autoclaving in a fermentation tank at 121° C. for 30 min. and allowed to cool to room temperature. Following sterilization, a nutrient feed was prepared by combining the following nutrients (prepared as described above): 10 ml glucose, 83.3 ml Hycase ® SF, 3.5 ml thiamine HCl, 2.5 ml vitamins, 2.5 ml trace elements, 25 ml adenine, 15 ml uracil, 12.5 ml yeast extract, and 12.5 ml peptone. The yeast seed was then added to the fermentation tank and cultured for a period of 5 hours. The yeast was then cultured at a temperature of 30° C. while a nutrient feed comprising 180 ml glucose, 75 ml Hycase ® SF, 22.5 ml yeast extract, 22.5 ml peptone, 31.25 ml yeast feed salts, 22.5 ml ethanol, 1.25 ml vitamins, 1.25 ml trace elements, 25 ml adenine, 3.0 ml thiamine, 10 ml uracil, 10 ml hisadine and 10 ml lysine (prepared as described above) was then added continuously at a rate of 0.11 ml/min for 20 hours, followed by a rate of 0.2 ml/min for an additional 24 hours. The final production medium composition was as follows:

The resulting yeast broth was centrifuged at 9,000 rpm for 10 minutes. The centrifuged supernatant was filtered through a 0.45 g filter and the clarified yeast broth was collected.

The MGF/IL-3 fusion protein was purified to homogeneity from the clarified yeast broth on a FLAG ® affinity column as instructed by the manufacturer (International Biotechnologies, Inc., New Haven, Conn.). Briefly, a FLAG ® affinity column was prepared and equilibrated with 1 mM CaCl$_2$, 0.1M HEPES, pH 7.5. The clarified crude yeast broth was pumped over the column, followed by a wash with equilibration buffer. The FLAG-MGF/IL-3 fusion protein was eluted from the affinity column with 0.1M sodium titrate, pH 3.0.

Example 4

Activity of MGF/IL-3 Fusion Proteins in Human Bone Marrow Colony Assay

The ability of MGF, IL-3 and fusion proteins comprising MGF and IL-3 to induce colony formation were compared in the following assays. In the first assay, granulocyte-macrophage colony- and cluster-forming cells (CFU-GM) were assayed by a procedure substantially similar to that described in Williams et al. *Exp. Hematol.* 15:243 (1987). Briefly, bone marrow cells were suspended in 0.5 ml of 0.3% agar (Difco, Detroit Mich.) or 0.4% agarose (FMC, Rockland, Me.) culture medium containing McCoy's 5A medium supplemented with essential and nonessential amino acids, glutamine, serine, asparagine, and sodium pyruvate (Gibco) with 20% fetal bovine serum. Quadruplicate cultures were incubated for seven days in a fully humidified atmosphere of 5% CO$_2$ in air. Colonies (>50 cells) and clusters (3–49 cells) were counted with an inverted microscope at 32×.

In the second assay, erythroid burst-forming units (BFU-E) and multipotential colony-forming cells (CFU-GEMM) were assayed by a procedure described in Williams et al., supra. Briefly, duplicate 35×10 mm cultures were stimulated with 2 units per ml of recombinant human erythropoietin (Hyclone), 0.1 mM hemin (Kodak), and 1000 U/ml IL-3 as a source of burst promoting activity. Cultures were incubated for seven days in a fully humidified atmosphere of 5% CO$_2$, 5% O$_2$ and 90% N$_2$. Maximal colony formation by murine BFU-E and CFU-GEMM was observed on day 14 using the foregoing culture conditions. BFU-E and CFU-GEMM were scored using an inverted stage microscope at 80× on the basis of hemoglobinization of erythroid elements, producing a characteristic red color, and the absence or presence of myeloid elements for the former and latter, respectively.

Using the foregoing assay, we compared the colony-forming activity of MGF, IL-3 MGF plus IL-3 and fusion proteins comprising MGF and IL-3 to control medium. The results are set forth in the following table:

TABLE A

| Cytokine | Dose (ng/ml) | Colonies/culture (Mean ± S.D.) | | |
|---|---|---|---|---|
| | | CFU-GM | BFU-E | CFU-GEMM |
| Control Medium | | 0 | 64 ± 4 | 0.5 ± 0.3 |
| MGF | 3 | 0 | 62 ± 2 | 0.8 ± 0.5 |
| IL-3 | 2 | 8 ± 1 | 104 ± 2 | 5.3 ± 0.6 |
| MGF + IL-3 | 2 + 3 | 14 ± 1 | 98 ± 4 | 6 ± 0.5 |
| PIXY523 | 4 | 10 ± 2 | 136 ± 4* | 14 ± 1* |
| | 12 | 36 ± 2 | 158 ± 5* | 31 ± 2* |

= value equal to media control
*p<0.05 compared to media control

These data indicate that MGF/IL-3 fusion proteins stimulate erythroid and primitive mixed colony formation. PIXY523 had significant BFU-E and CFU-GEMM stimulatory activity over controls and over MGF and IL-3 alone and MGF and IL-3 combined.

Example 5

Activity of MGF/IL-3 Fusion Proteins in Human Peripheral Blood Expansion Assay An experiment was conducted to compare the expansion ratios for human hematopoietic progenitor cells expanded ex vivo with progenitor expansion media comprising different growth factors or growth factor combinations or media without added growth factors.

Human peripheral blood was obtained from normal, healthy, volunteers via veinipuncture and collected in a heparinized tube. Mononuclear cells were obtained from peripheral blood by density gradient centrifugation on Histopaque ® (Sigma, St. Louis). The mononuclear cells, containing a population of human hematopoietic progenitor cells were washed twice in phosphate buffered saline (PBS) and viable cells counted by trypan blue dye exclusion.

Ex vivo cultures were made from approximately $10^7$ viable cells in 10 ml of Super McCoys medium supplemented with 20% fetal bovine serum. Cells were cultured and expanded in petri dishes incubated at 37° C. in an atmosphere of 7% $CO_2$, 8% $O_2$, 85% air. Culture media were replaced on day 4 with new growth factor(s).

Growth factors were added to media at the following concentrations: PIXY321 (100 ng/ml), MGF (1 µg/ml), IL-3 (100 ng/ml), PIXY 523 (1 µg/ml).

Progenitor cells in culture tend to be nonadherent. For each colony assay, 50% of nonadherent cells in each culture were obtained. Cells were separated from media by centrifugation, washed twice and viable cells counted by trypan blue due exclusion.

A CFU-GM assay (Lu et al., *Exp. Hematol.* 13:989, 1985) measured a myeloid component of the progenitor cell population. Viable cells were plated in a methyl cellulose cloning media (Terry Fox Labs, Vancouver, B.C.) in the presence of PIXY32 1 (GM-CFU). The number of myeloid colonies were counted and this number was divided by the number of cells plated into each well to determine a colony-forming capacity (CFC) incidence. CFC incidence was multiplied by total cell number to determine CFC number per culture. Each CFC number was compared to a day 0 CFC number to determine an expansion ratio for each progenitor expansion media tested.

Myeloid component cell expansion was determined after 4 and 8 days of incubation with growth factors MGF, IL-3, PIXY321, PIXY523 and combinations of these growth factors. An expansion number of 1 means that there was no expansion of colony number, whereas an expansion number of 2 means that the number of colonies doubled from the day 0 number.

TABLE B

Colony Forming Activity of Cytokines Including MGF

| Cytokine | CFU-GM Expansion Index | |
|---|---|---|
| | Day 4 | Day 8 |
| Medium | 0.5 | 0.7 |
| MGF | 1.2 | 1.1 |
| IL-3 | 2.0 | 3.6 |
| PIXY321 | 2.2 | 4.8 |
| PIXY523 | 3.2 | 9.2 |
| IL-3 + MGF | 2.6 | 4.2 |
| PIXY321 + MGF | 4.0 | 7.0 |

These data indicate that PIXY523 stimulates the production of granulocyte-macrophage colony forming cells to a significantly greater degree than the medium control or either MGF or IL-3 alone or in combination. At day 8, PIXY523 also had a greater expansion index relative to PIXY321 plus MGF.

I claim:

1. A fusion protein comprising MGF linked to IL-3, wherein MGF and IL-3 are linked via a C-terminal to N-terminal fusion.

2. A fusion protein according to claim 1, wherein MGF is linked to IL-3 via a linker peptide sequence.

3. A fusion protein according to claim 2, wherein said linker peptide sequence comprises am